US010493452B2

(12) United States Patent
Burger et al.

(10) Patent No.: US 10,493,452 B2
(45) Date of Patent: Dec. 3, 2019

(54) MICROFLUIDIC DEVICE

(71) Applicant: QMICRO B.V., Enschede (NL)

(72) Inventors: Gerardus Johannes Burger, Enschede (NL); John Gerhardus Maria Bijen, Enschede (NL); Dionysius Antonius Petrus Oudejans, Enschede (NL); Harm Jan Weerden, Enschede (NL)

(73) Assignee: QMICRO B.V., Enschede (NL)

( * ) Notice: Subject to any disclaimer, the term of this patent is extended or adjusted under 35 U.S.C. 154(b) by 66 days.

(21) Appl. No.: 15/746,928

(22) PCT Filed: Jun. 22, 2016

(86) PCT No.: PCT/EP2016/067578
§ 371 (c)(1),
(2) Date: Jan. 23, 2018

(87) PCT Pub. No.: WO2017/017032
PCT Pub. Date: Feb. 2, 2017

(65) Prior Publication Data

US 2019/0134627 A1 May 9, 2019

(30) Foreign Application Priority Data

Jul. 24, 2015 (NL) ...................................... 1041407

(51) Int. Cl.
*B01L 3/00* (2006.01)
*G01N 15/06* (2006.01)
(Continued)

(52) U.S. Cl.
CPC ... *B01L 3/502707* (2013.01); *B01L 3/502715* (2013.01); *B01L 2200/025* (2013.01);
(Continued)

(58) Field of Classification Search
CPC .......... B01L 3/00; G01N 15/06; G01N 33/00; G01N 33/48
(Continued)

(56) References Cited

U.S. PATENT DOCUMENTS

| | | | |
|---|---|---|---|
| 5,932,315 | A | 8/1999 | Lum et al. |
| 6,399,178 | B1 | 6/2002 | Chung |

(Continued)

FOREIGN PATENT DOCUMENTS

| | | | |
|---|---|---|---|
| CN | 101405084 | A | 4/2009 |
| CN | 102371194 | A | 3/2012 |

OTHER PUBLICATIONS

Chinese Office Action for family member application dated Nov. 2, 2018, with translation.

*Primary Examiner* — Brian J. Sines
(74) *Attorney, Agent, or Firm* — Hudak, Shunk & Farine Co. LPA

(57) ABSTRACT

Substrate for a microfluidic device, including at least one microfluidic structure having at least one access port at an upper surface of the substrate, a raised support structure positioned on the upper surface adjacent to each access port and surrounding the access port, the raised support structure partially covering the substrate upper surface, the first raised support structure having an upper surface for receiving an adhesive for mounting a microfluidic component having at least one access port corresponding to the at least one access port of the substrate. A microfluidic device, including a substrate, a microfluidic component having at least one access port at a lower surface corresponding to the at least one access port of the substrate. The microfluidic component is mounted on the top of the substrate with an adhesive applied between the upper surface of the at least one first
(Continued)

and/or second raised support structure and the lower surface of the microfluidic component.

20 Claims, 5 Drawing Sheets

(51) Int. Cl.
*G01N 33/00* (2006.01)
*G01N 33/48* (2006.01)

(52) U.S. Cl.
CPC . *B01L 2200/027* (2013.01); *B01L 2200/0689* (2013.01); *B01L 2200/12* (2013.01); *B01L 2300/0645* (2013.01); *B01L 2300/0874* (2013.01); *B01L 2300/0887* (2013.01)

(58) Field of Classification Search
USPC .................. 422/68.1, 502, 503, 504; 436/43
See application file for complete search history.

(56) References Cited

U.S. PATENT DOCUMENTS

| | | | |
|---|---|---|---|
| 8,383,060 | B2 | 2/2013 | Dekker et al. |
| 8,916,111 | B2 | 12/2014 | Wimberger-Friedl et al. |
| 2002/0127149 | A1 | 9/2002 | Dubrow et al. |
| 2003/0106799 | A1* | 6/2003 | Covington ........ B01L 3/502707 204/600 |
| 2004/0028566 | A1 | 2/2004 | Ko et al. |
| 2005/0048669 | A1* | 3/2005 | Hobbs ................ G01N 30/6026 436/180 |
| 2005/0284213 | A1* | 12/2005 | Karp ................ B01L 3/502715 73/61.52 |
| 2006/0124230 | A1 | 6/2006 | Chartier et al. |
| 2009/0010805 | A1* | 1/2009 | Raynor ............... B01L 3/50273 422/68.1 |
| 2009/0129986 | A1 | 5/2009 | Wimberger-Friedl et al. |
| 2010/0068105 | A1* | 3/2010 | Green .................. B01J 19/0093 422/600 |
| 2012/0024396 | A1 | 2/2012 | Ehrenpfordt et al. |
| 2012/0089180 | A1 | 4/2012 | Fathi et al. |

* cited by examiner

MICROFLUIDIC DEVICE

FIELD OF THE INVENTION

The invention relates to a microfluidic device, a substrate for a microfluidic device and a method of manufacturing a microfluidic device.

BACKGROUND OF THE INVENTION

Microfluidic devices are devices which are capable of handling small amounts of chemical, bio-chemical or biological substances, i.e. for the analysis thereof. Microfluidic devices may comprise microfluidic channels, valves and other structures, including sensors and electronic circuitry to operate. Complex structures can be built on for example semiconductor components having dimensions in the order of micrometers.

Microfluidic devices can be built in a two-part form having a micromachined substrate and a microfluidic component mechanically, fluidically and electrically connected to the substrate. The substrate usually comprises a micromachined channel plate. The microfluidic component usually comprises a micromachined fluidic chip. A common method of mounting the microfluidic component on the substrate is called Flip-chip technology. In Flip-chip technology mechanical, microfluidic and electrical structures present in the substrate and microfluidic component can be connected by mutually corresponding connections in the surfaces of the respective parts facing each other. Such connections include corresponding access ports of microfluidic channels which run through the substrate and extend in the microfluidic component, and mechanical and electrical connections.

Microfluidic devices can be used beneficially in high temperature applications such as gas chromatography, where robustness of the fluidic and electrical connections when subjected to temperature variations plays a key role. In such applications, the fluidic connections should normally be gas tight, typically up to 5 bar with no or very low leak rates, and the electrical connections should be low ohmic. The temperature range over which the assembly should stay intact is typically −20 to +200 C.

In order to make the mechanical and fluidic connection as described, the microfluidic component and substrate can be connected using an adhesive layer. An adhesive layer can be formed by using a preformed layer sandwiched between the substrate and microfluidic component, or by applying an adhesive to mechanical structures designated for mechanically connecting the parts together. The electrical connection can be made by using conductive bumps for example gold bumps which are sandwiched between corresponding contact pads between the two facing surfaces. The conductive bumps electrically bond the respective contact pads when the microfluidic component is mounted on the substrate.

Microfluidic devices generally may have dimensions in the order of 3-15 mm, however larger or smaller dimensions may apply. Electrical connections in microfluidic devices can be normally sized in a range of 50-300 micrometer, whereas microfluidic access ports can be sized in a range of 50-1500 micrometer. With such small dimensions, microfluidic access ports and their associated channels acts as capillaries. Adhesively connecting the microfluidic component to the substrate with structures having such small dimensions requires the application of adhesive to be patterned and accurately aligned between the substrate and microfluidic component. Misalignment and excess adhesive may cause an overflow of adhesive from the mechanical connecting structures to functional parts of the substrate and/or microfluidic components due to their capillary action, thereby adversely affecting their function. One way to solve this is by applying adhesive in the form of a patterned adhesive preform. However, this requires an additional component, i.e. the preform, which also requires accurate patterning, positioning and aligning. Moreover, creating an adhesive bond in this manner requires exerting a considerable pressure to the microfluidic components and substrate, which may result in mechanical stress or even damage to either of the microfluidic parts. A further disadvantage is that air may become trapped between preform and component surfaces during assembly, resulting in poor adhesion properties. In the art gaskets have been used for sealing off microfluidic channels and preventing sealant, i.e. adhesive to spill into these channels and ports, impairing the microfluidic function and integrity. The use of gaskets also requires separate components, i.e. the gaskets, which also require positioning and aligning. Moreover, such gaskets require mechanical stress to perform the required sealing.

Furthermore, in the art, as described for example in U.S. Pat. No. 8,916,111, adhesive is applied in cavities between a substrate and a microfluidic component as an underfill for providing additional bonding strength between these parts. This solution however is not compatible with the required robustness with respect to temperature variations. Differences between thermal expansion coefficients between the adhesive used for this purpose and the material of the substrate may cause mechanical tension between the substrate and the microfluidic component and cause subsequent release of the bond and/or leaking of microfluidic structures within the substrate or microfluidic component. Also air bubbles trapped in the relatively thick adhesive layer, i.e. underfill, within the cavities may expand and cause breaking of the bond between substrate and microfluidic component bonded to the substrate during thermal cycling. This is sometimes referred to as popcorn effect. Delaminarion or peel-off of the microfluidic component starts off with a local release which is then propagated throughout a larger part of the adhesive layer between the substrate surface and microfluidic component.

In case of a combination of fluidic and electrical connections, thermal stress will occur since materials used in contact bumps for electrical connection, such as gold, and silicon have different thermal expansion coefficients. In general, there is a risk is that the electrical connection will be lost due to too high stress in the gold bumps.

SUMMARY OF THE INVENTION

It is an object of the invention to overcome the problems and disadvantages as stated above. The object is achieved in a substrate for a microfluidic device. The substrate comprises at least one microfluidic structure having at least one access port at an upper surface of the substrate, and a first raised support structure positioned on the upper surface adjacent to each access port and surrounding the access port. The first raised support structure partially covers the substrate upper surface. The first raised support structure has an upper surface for receiving an adhesive for mounting a microfluidic component having at least one access port corresponding to the at least one access port of the substrate.

An access port is an opening in either the substrate upper surface or the microfluidic component lower surface which provides fluidic access to its microfluidic structure on or within the substrate body of component body respectively. A microfluidic structure can include a microfluidic channel, duct, a sensor, a valve, etcetera.

The surrounding of the at least one access port by the first raised support structure is preferably in an uninterrupted manner, leaving no lateral openings. This is for sealing off the access ports and thereby sealing off the associated microfluidic channels from the substrate surface.

After application of the adhesive, the microfluidic component can subsequently be mounted on top of the adhesive layer. The microfluidic component has corresponding ports in the lower surface, matching with the ports of the substrate. This also called flip-chip design. An advantage of this solution is that the adhesive can be applied on these surfaces without aligning. The microfluidic component needs to be aligned with the raised support structures when mounting, so the applying of the adhesive is relatively straight forward. Flow of adhesive is limited to the upper surface of the raised support structure, thus preventing overflow to functional parts of the substrate and/or microfluidic components.

After mounting, the raised support structures and adhesive together form the mechanical and fluidic connection between substrate and microfluidic component. Moreover, the raised support structure and adhesive form a sealed connection between the corresponding ports of the substrate and microfluidic component.

In addition to the first raised support structures, the substrate further comprises

- a pattern of at least one second raised support structures having substantially a same height as the raised support structure, the at least one second raised support structure having an upper surface for receiving the adhesive for mounting the microfluidic component, wherein
- the pattern occupies a portion of the upper surface of the substrate not covered by the second raised support structure and/or the at least one access port.

The second raised support structures, i.e. additional bumps, provide additional mechanical support for the microfluidic component to be mounted on top of the substrate. The second raised support structures do not provide sealing to a fluidic connection between corresponding ports. The second raised support structures can have a square, rectangular or round shape as viewed in a top view. Round shaped second raised support structures or bumps might even perform better considering induced stress and adhesive application.

The pattern of second raised support structures provides spreading of mechanical tensions across the substrate surface. By applying the same adhesive as in the first raised support structures, no further adhesive is required in cavities between the substrate and microfluidic component for providing sufficient bonding thereof. Thus mechanical stress due to uneven or unequal expansion coefficient between the further adhesive and the substrate material is prevented.

A minimal amount of adhesive is applied on top of the second raised support structures directly, thus no flow of adhesive towards areas where bonding needs to be effected is necessary. Thereby contamination, premature curing, undesired filling up of cavities, etc. is prevented. Since the adhesive contact areas are small and the distance to an adhesive edge is short enclosure of air in the adhesive layer is much less likely. Since no under fill is used the pressure between the bumps is always released to ambient pressure In an embodiment, the raised support structure has a width and a height. The width has a dimension preferably in a range of 1-10 times the height dimension.

In an embodiment, the pattern of at least one second raised support structure comprises grooves between the second raised support structures. Grooves can easily be created by for example lithography, etching, laser ablation or other techniques, achieving micrometer precision with respect to dimensions, wherein top surface material of the substrate is removed to form the grooves. The grooves prevent air to become trapped in air pockets between the assembled components. Due to the grooves in the pattern of second raised support structures, the pattern has a discontinuous or interrupted character. Large surface areas are avoided. Thus the risk of peel-off through propagation of a local fault in the adhesive bond between substrate and microfluidic component is reduced, as a local fault may be stopped at a groove.

In an embodiment, the pattern is preferably substantially a regular pattern, providing uniform distribution of mechanical tensions across the substrate surface.

The raised support structure provides an offset for the adhesive, thereby reducing the amount of adhesive necessary for establishing a secure bond between the substrate and the microfluidic component. The adhesive can be globally applied in a thin layer across the raised support structures of the upper surface of the substrate. The reduced amount of adhesive prevents the adhesive to spill into the ports and block microfluidic structures within the substrate and/or component. Moreover, the offset obviates the need for preformed, patterned adhesive sheets which are commonly used in bonding substrates with microfluidic components. Such patterned sheets require extensive aligning with the substrate, whereas the raised support structures only require application of an adhesive which can be performed by a single application operation on the overall top surface, i.e. top surfaces of the raised support structures, of the substrate.

In an embodiment, the substrate material is a preferably a semiconductor material. A preferred material is silicon. Silicon is strong, durable, is very low corrosive and allows creation of highly accurate micro- or even nanostructures.

Other materials can also be considered. Important is that the substrate material is a low corrosive material. This prevents interaction of the substrate with fluids, i.e. liquids or gasses, coming in contact with substrate surfaces.

Examples of low corrosive substrate materials are glass, quartz, plastic, epoxy. In glass or quartz fine microfluidic structures can be created, however with less accuracy than in silicon. Plastics and epoxies allow the mass manufacturing of low cost devices for applications for specific fluids.

In another aspect, a microfluidic device is considered. The microfluidic device, comprises:

- a substrate as described above,
- a microfluidic component having at least one access port at a lower surface corresponding to the at least one access port of the substrate upper surface,
- the microfluidic component being mounted on the top of the substrate with an adhesive applied between the upper surface of the at least one first and/or second raised support structure and the lower surface of the microfluidic component.

The combined structure provides the advantages as described above.

In the microfluidic device, structures of the substrate upper surface match with corresponding structures of the microfluidic component bottom surface in accordance with flip-chip technology.

In an embodiment, the adhesive is preferably applied between the upper surface of the at least one first and/or second raised support structure and a corresponding surface of the microfluidic component only. This leaves free space between the raised support structures, allowing excess air to be released when the microfluidic component is mounted on top of the substrate. The releasing of excess air also prevents the forming of air bubbles within the adhesive.

In an embodiment, the adhesive can be chosen from a group of adhesives comprising epoxies, polyimide, high temperature ceramic adhesives, spin-on glass and glass frit, depending on the type of microfluidic device and fluid to be handled by the microfluidic device. Epoxies provide adequate sealing at low temperatures in chemically friendly environments, i.e. fluids, whereas high temperature ceramic adhesives provide more adequate sealing for high temperature applications. Spin-on glass provides the advantages of being soluble in water allowing easy application on the support structure upper surfaces. Hence after thermal treatment, optimal sealing and anticorrosion are achieved. Even better results are achieved using glass frit, which can be applied onto the raised support structures upper surfaces in a paste form. After thermal treatment optimal sealing and mechanical bonding is achieved. As the adhesive can be applied as a thin layer between raised structures of the substrate and corresponding structures of the microfluidic device, a strong reliable mechanical and fluidically sealed connection is made. The need for highly accurately aligning adhesive application or adhesive preform alignment is obviated, whereas integrity of fluidic ports an channels is maintained, obviating a need for gaskets.

In an embodiment, the microfluidic device further comprises an electrical connection of the substrate and the microfluidic component, the electrical connection comprising a contact bump, pressed between a contact pad of the substrate and a contact pad of the microfluidic component, wherein the adhesive layer has a thickness, wherein the thickness of the adhesive layer and a height of the at least one second raised support structure is adjusted to a size of the contact bump. The thickness of the adhesive layer on the raised support structures can be used to regulate the stress in the contact bumps due to thermal expansion. In general, adhesive layers have a low modulus of elasticity while silicon as a high modulus of elasticity. The contact bump has a modulus of elasticity somewhere in between. This makes it possible to tune the thickness of the adhesive layer such that the resulting stress is close to zero independent of the temperature. The thickness of the adhesive layer can be controlled using a proper application process or by using spacer particles mixed into the adhesive.

In an embodiment, the contact bump is made of gold.

In an embodiment, the contact pad of the substrate is arranged on a raised support structure. In this case, when using anisotropically conductive adhesive (i.e. an adhesive containing conducting particles), an electrically conductive path is formed in areas having contact pads on the substrate and the microfluidic component which are pressed onto each other (on top of the raised support structures) while in the other area's there is no electrical conduction.

In an embodiment, the contact bumps are made of resilient material on which the conductive layer is provided. The adhesive layer thereby sustains any un evenness of the surfaces between which the adhesive is applied by elastic compression of the contact bumps.

Exemplary embodiments of the invention will be further elucidated in the drawings set out below.

Examples of embodiments of the invention will be further elucidated in the description set out below.

DETAILED DESCRIPTION OF THE INVENTION

Figure 1A:
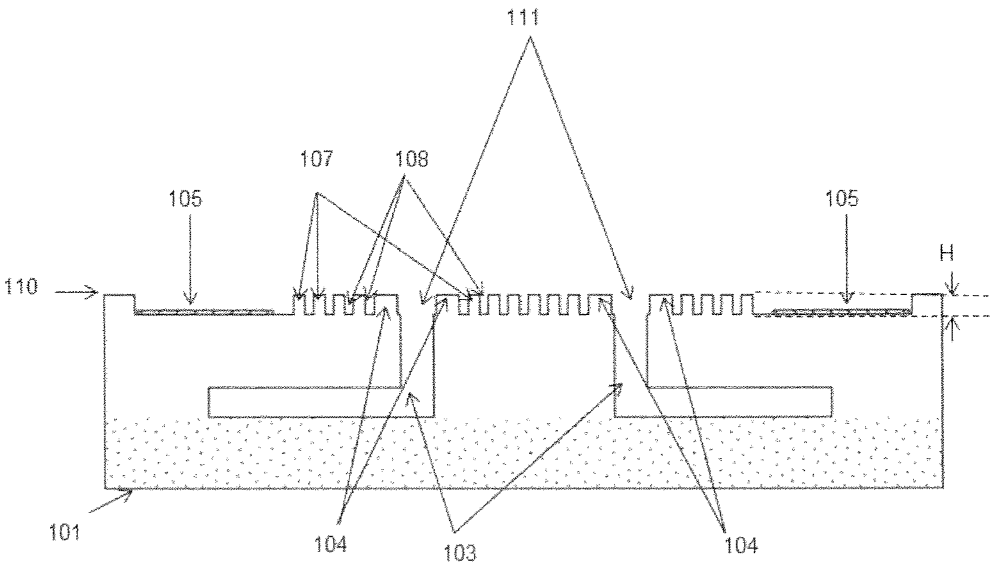
FIG. 1A shows a cross-section of a substrate of the microfluidic device according to an embodiment of the invention.

FIG. 1A shows an example of a substrate 101 which can be used in a microfluidic device. The substrate 101 can be provide with microfluidic channels 103 which can have microfluidic inputs and/or outputs, not shown in FIG. 1A. The microfluidic channels have access ports 111 at the top surface 110 of the substrate 101.

The substrate 101 may further include microfluidic sensors and/or other microfluidic components, not shown in FIG. 1A. The substrate 101 is provided with contact pads 105 for electrically connecting electronic or electromechanical components within the microfluidic device to for example power-supplies, electronic control circuits and other electrical of electronic equipment.

The substrate 101 can be manufactured from semiconductor materials including silicon, germanium, gallium arsenide, ceramics, polymers and similar materials. Alternatively, the substrate material can be glass. Structures within the respective parts 101, 201 can be made by methods and techniques known to the skilled person. The raised support structures 104 can for example be created by etching away substrate surface material. The raised support structures 104 remain as a consequence. The raised support structures 104 have top surfaces which can be provided with an adhesive for attaching a microfluidic component such as a microfluidic chip on top of the substrate 101 to create the microfluidic device.

In order to improve the mechanical bonding of the substrate 101 and microfluidic component, micro bumps 107 can be created as additional raised support structures on top of the upper surface 110 of the substrate 101, independent from the raised support structures 104 surrounding the access ports. These micro bumps 107 also have top surfaces which can be provided with an adhesive for attaching the microfluidic component to the substrate 101.

As shown in FIG. 1A, the micro bumps 107 can be created by creating grooves 108 between the respective support structure 107. Likewise this applies to grooves 108 being created between raised support structures 104 and raised support structures 107.

The raised support structures 104 and micro bumps 107 are shown having a height H. The respective heights of these structures 104, 107 may differ.

Figure 1B:
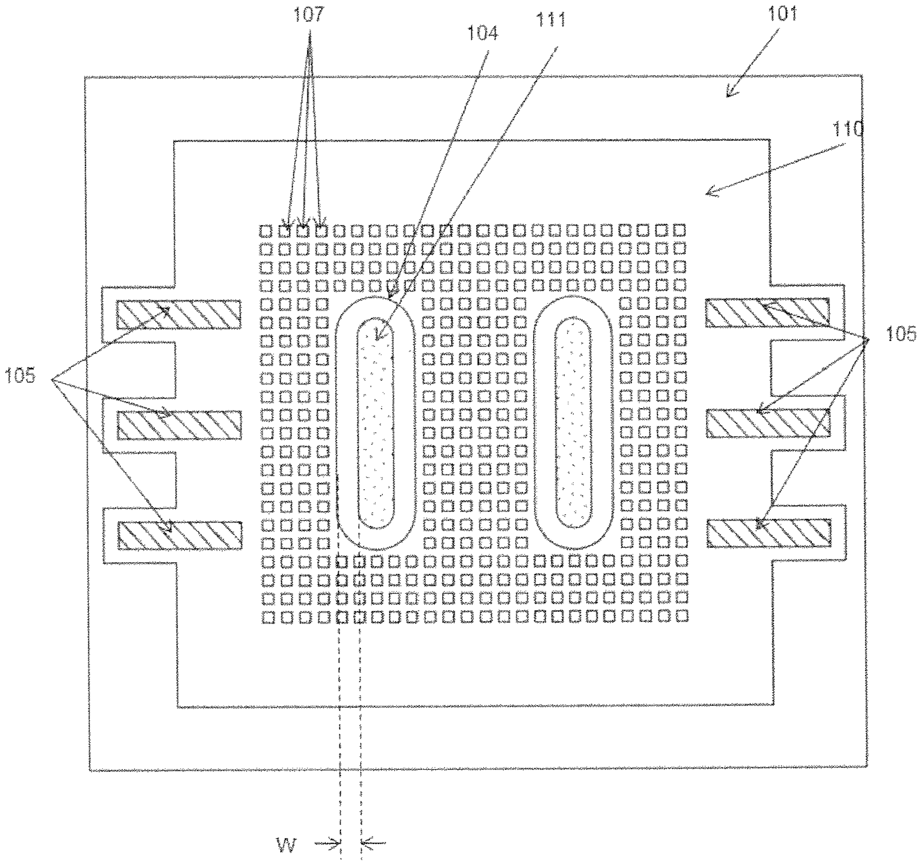
FIG. 1B shows a top view of the substrate according to FIG. 1A.

FIG. 1B shows a top view of the substrate according to FIG. 1A. The raised support structures 104 surround the access ports 111. The raised support structures 104 have a width W typically of the same order as the smallest width of the access port 111. This allows for small amounts of adhesive to be applied to the raised support structures top surfaces for attaching the microfluidic component while achieving a strong bonding between the substrate 101 and the microfluidic component, relative to applying the adhesive to the top surface of the substrate corresponding to the microfluidic bottom surface being in touch with the substrate 101. The same applies to width of the micro bumps 107, which provide additional strength in bonding the microfluidic component to the substrate 101, while requiring relatively low amounts of adhesive. Preferably a width of the support structures 104, 107 is chosen which provides sufficient bonding force with minimum use of contact area. The width W/height H ratio of the raised support structures 104, 107 typically vary in a range of 1-10, providing sufficient stability and top surface area for applying adhesive. For more stability of the connection between substrate and microfluidic device, the additional support structures are typically evenly distributed across the substrate top surface 110 at locations not occupied by raised support structures 104 for delimiting access ports 111. The additional raised support structures can be arranged on the substrate surface 110 in a regular pattern, such as for example a rectangular pattern as shown in FIG. 1B. This allows any force applied to a microfluidic component mounted on top of the substrate 101 to be distributed evenly on the substrate 101.

Figure 2A:
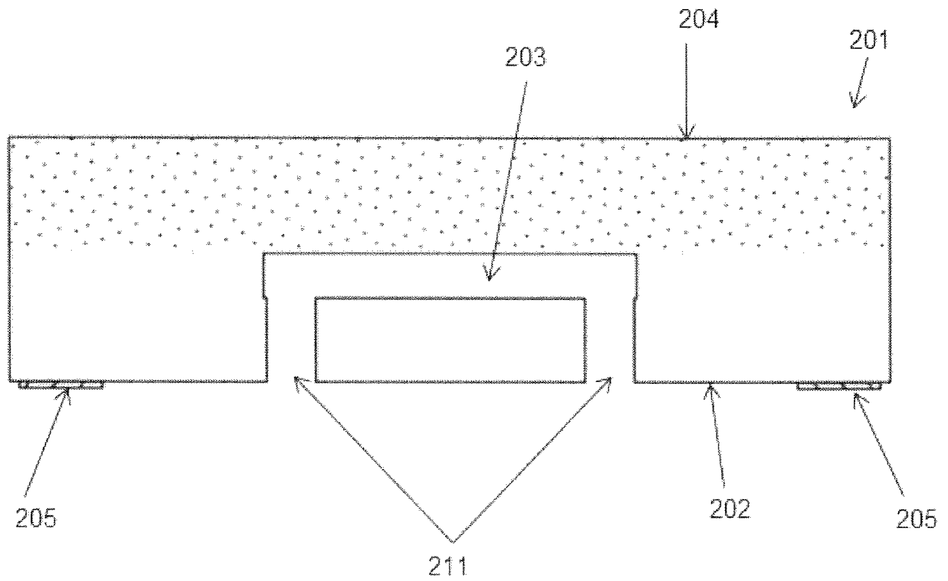
FIG. 2A shows a cross-section of a microfluidic component of a microfluidic device according to an embodiment of the invention.

FIG. 2A shows a cross-section of a microfluidic component of a microfluidic device according to an embodiment of the invention. Like the substrate 101, the microfluidic component 201 may have microfluidic channels 203, microfluidic sensors and/or other components for performing its microfluidic function. Electrical connection is made via contact pads 205 which can be connected to corresponding contact pads 105 on the substrate 101 using for example conductive bumps.

Figure 2B:
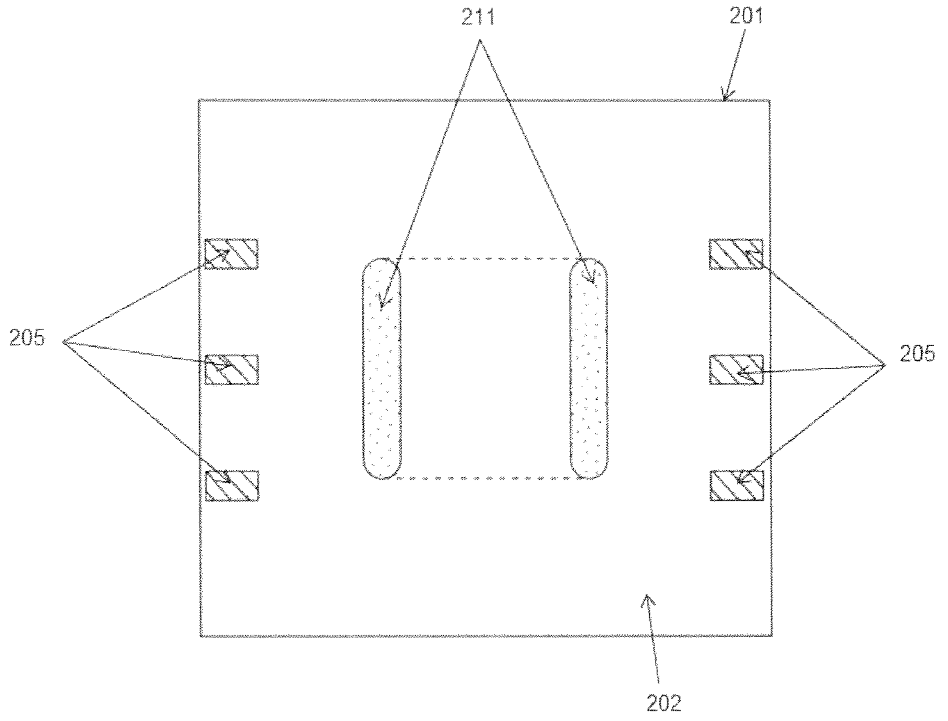
FIG. 2B shows a top view of the microfluidic component of FIG. 2A.

FIG. 2B shows a bottom view of the microfluidic component of FIG. 2A. The lower surface 202 is to be bonded with the top surface 110 of the substrate 101. The access ports 211 correspond to the access ports 111 of the substrate.

Figure 3A:
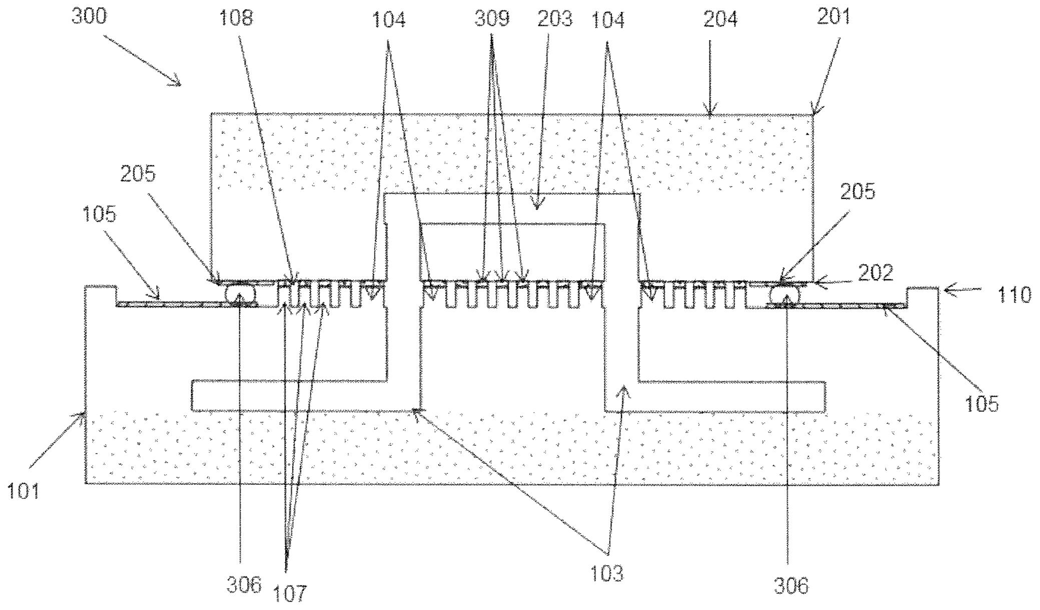
FIG. 3A shows a cross-section of a microfluidic device according to an embodiment of the invention.

FIG. 3A shows a cross-section of a microfluidic device 300 comprising the substrate 101 and the microfluidic component 201 as described above.

Conductive bumps 306 provide electrical connection between the contact pads 105 of the substrate and the corresponding contact pads 205 of the microfluidic component. The conductive bumps 306 can be in the form of gold bumps. Alternative means of electrical connecting and bonding can be considered, e.g. solder bumps or solder preforms.

All dimensions of features 103-108, of the described substrate 101 are in a typical micromachining range, e.g. in the order of 1-1500 micrometer. The top surfaces of the raised support structures 104 and micro bumps 107 are provided with a thin layer of adhesive 309, which may have a thickness in the order of 2-10 micrometer.

The substrate and microfluidic component 201 are mechanically and fluidically connected and fluidically sealed by means of the adhesive layer 309 on the raised support structures 104 top surfaces which are positioned and aligned with access ports 211 of the microfluidic channels 203 of the microfluidic component 201. In practice, the height and width of the support structure 104 can be in the order of 5-250 micrometer and the thickness of the adhesive layer 309 can be in the order of 2-10 micrometer. The height of the microstructure can be adapted to the size of the conductive bumps 106 or vice versa.

Adhesives include epoxies, high temperature ceramic adhesives and glass frit. These adhesives can be globally applied to the top surfaces of the raised support structures 104, 107, without requiring extensive positioning and/or aligning. The adhesive can for example be applied by means of transfer printing. The amount and viscosity of the adhesive to be applied is chosen such that the grooves 108 between the raised support structures 104, 107 remain open. This reduces mechanical tension between the substrate 101 and microfluidic component 201 and it allows for excess air to escape while bonding the microfluidic component 201 to the substrate 101. Also blocking of the access ports 111, 211 is prevented in the same manner.

Only a relatively low amount of adhesive needs to be applied on top of the raised support structures 104. This prevents excess adhesive to flow into the access ports 111 of the underlying microfluidic channels 103. The relative low amount of adhesive on top of the additional raised support structures also allow excess air between the raised support structures 104, 107 and the microfluidic component lower surface 202 to escape while mounting the microfluidic component 201 to the substrate 101, ensuring a uniform bonding between the microfluidic component and the top surface 110 of substrate 101, without bubbles.

Figure 3B:
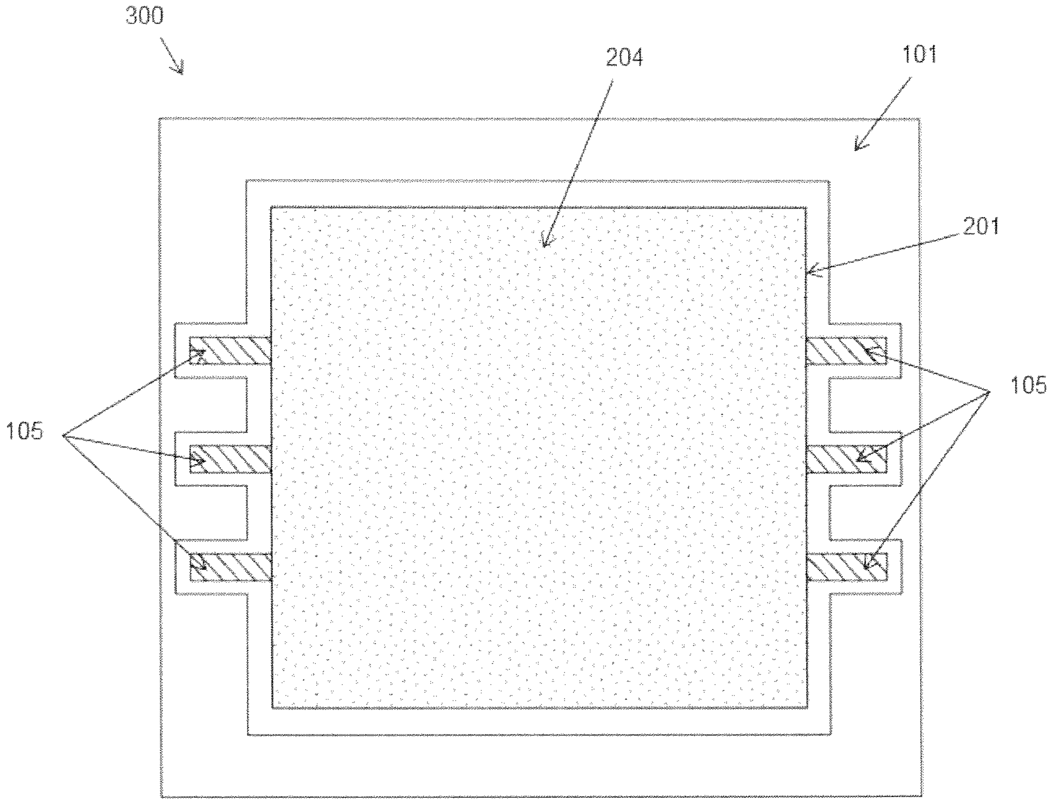
FIG. 3B shows a top view of the microfluidics component of FIG. 3A.

FIG. 3B shows a top view of the microfluidic device 300 of FIG. 1A. It shows the top surface 110 of the substrate 101 and top surface 204 of the microfluidic component 201 as it is mounted on the substrate 101. The contact pads 105 of the substrate 101 are exposed for electrically supplying and controlling the microfluidic device 300. Not shown on the top surface 110 of the substrate 101 are microfluidic inputs and outputs, for microfluidically attaching the microfluidic channels 103 of the device 300 to further devices and/or equipment.

Figure 4A:
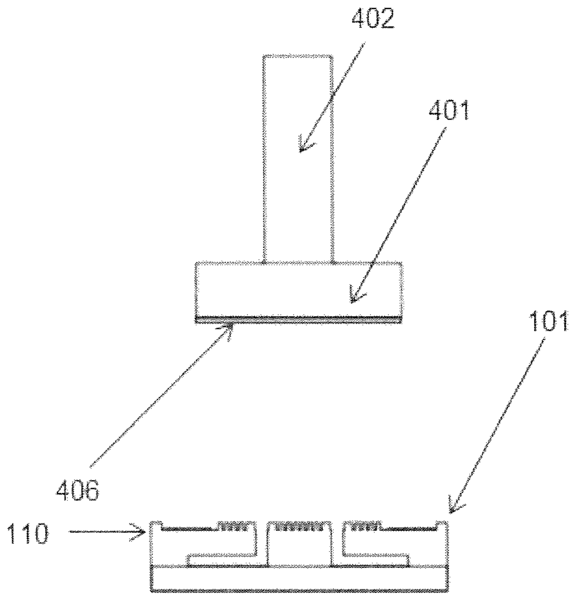
FIG. 4A-4B show a method of manufacturing microfluidic device 300 according to an embodiment of the invention.

FIG. 4A shows an exemplary method 400 for applying layer of adhesive 404 to the substrate upper surface 110. The adhesive is applied to a rotatable stamp 401, for example by means of an adhesive dispenser. The amount of adhesive, i.e. adhesive layer thickness can be example be determined by spinning the stamp 401 with a speed and time as required to achieve the desired thickness and evenness.

FIG. 4A an amount of adhesive 406 is shown which is evenly spread across the bottom surface of a stamp 401, while the stamp 401 is being positioned above the top surface of the substrate 101.

Figure 4B:
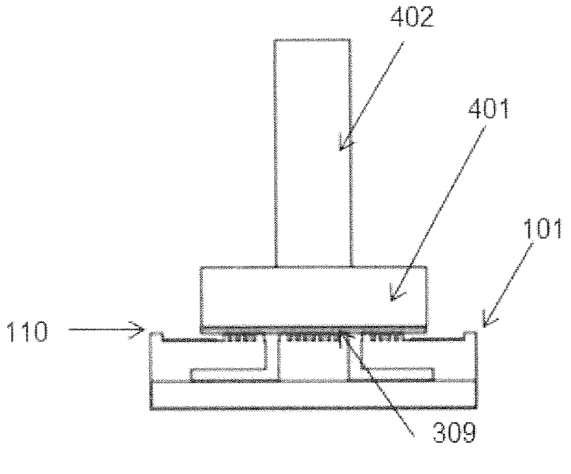

In FIG. 4B is shown that the stamp 401 can be lowered towards the substrate upper surface 110 such that the adhesive 406 at the bottom surface of the stamp 401 can be transferred onto the top surfaces of the raised support structures 104, 107 forming the adhesive layer 309 for bonding a microfluidic component 201 to the substrate 101 as is shown in FIG. 3A.

The microfluidic component 201 can be mounted on top of the adhesive layer 309 which is applied on the upper surfaces of the raised support structures 104, 107 of the substrate 101. The microfluidic component 201 can be positioned and aligned relative to the substrate top surface 110 and placed on top of the substrate 101 using for example a robotic arm fit for positioning and aligning semi-conductor devices, thus arriving at a device in accordance with FIGS. 3A and 3B.

While mounting the microfluidic component 201 on top of the substrate 101, a certain amount of pressure is exerted on the microfluidic component 201 in order for the adhesive to contact the lower surface 202 of the microfluidic component 201 to ensure full contact of the lower surface 202 with the adhesive in the adhesive layer 309. Simultaneously with the mechanical and fluidic connection, the exerted pressure also allows electrical connection to be bonded between the overlapping parts of contact pads 105, 205 of the substrate 101 and microfluidic component 201 respectively by compressing the contact bumps 306 between the overlapping parts of contact pads 105, 205.

Figure 5A:
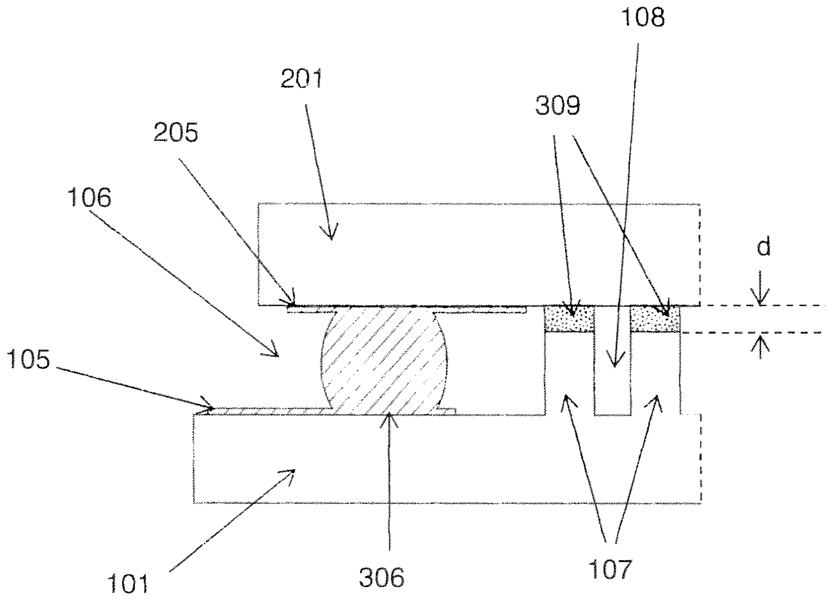
FIG. 5A shows a detail of a cross section of a microfluidic device according to an embodiment of the invention.

In FIG. 5A an example of an electrical connection is shown at an edge of the microfluidic device 100, between the substrate 101 and the microfluidic component 201. A contact bump 306 is shown between the contact pads 105 and 205 of the substrate 101 and the microfluidic component 201 respectively. A thickness h of the adhesive layer 309 is chosen such that it matches with the contact bump 306 size, which is shown in a compressed state in FIG. 5A, and the size of the raised support structures such that the resulting thermal stress is minimized.

In FIG. 5A an example of an electrical connection 106 is shown at an edge of the microfluidic device 100, between the substrate 101 and the microfluidic component 201. A contact bump 306 is shown between the contact pads 105 and 205 of the substrate 101 and the microfluidic component 201 respectively. A thickness d of the adhesive layer 309 is chosen such that it matches with the contact bump size. The contact bump 306 in FIG. 5A is shown in a compressed state due to pressing the microfluidic component 201 on top of the substrate 101.

Figure 5B:
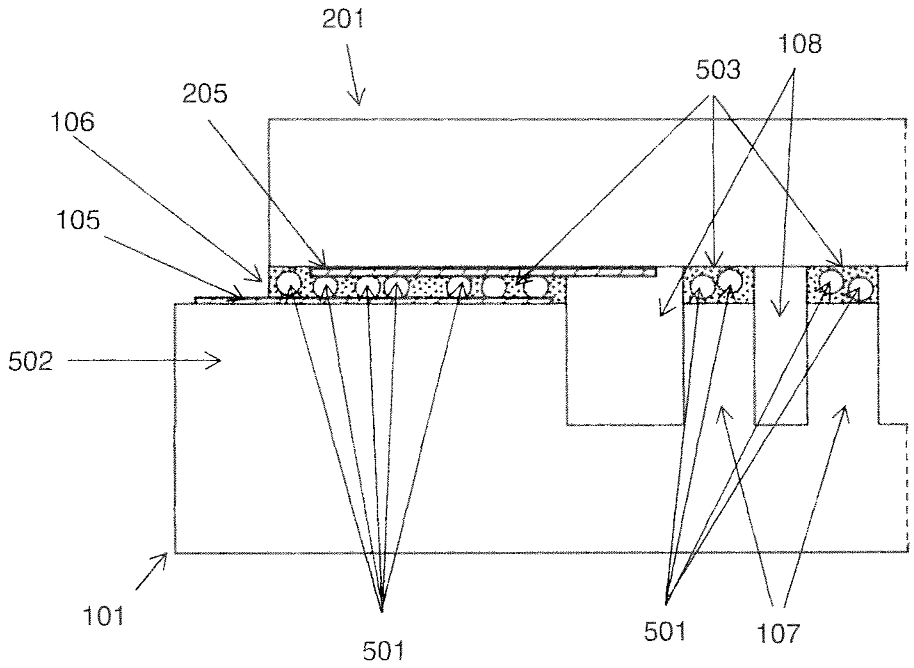
FIG. 5B shows another detail of a cross section of a microfluidic device according to an embodiment of the invention.

In FIG. 5B an alternative approach for establishing the electrical connection 106 is shown. The multiple contact bumps 501 are previously distributed within the adhesive layer 309. The contact bumps 501 are provided with a conductive outer layer. The substrate contact pad 105 is arranged on a raised contact support structure 502 at the edge of the substrate 101. Adhesive 503 with the contact bumps 501 is applied on the top surface of the substrate 101, causing the exposed surfaces on top of the micro bumps 107 and the raised contact support structure 502 and contact pad 105 to be covered with adhesive with the contact bumps 501. The grooves 108 remain clear of adhesive. When the microfluidic component 201 is positioned on top of the substrate, the contact bumps 501 within the adhesive layer act as spacers near the micro bumps 107, and provide electrical contact between the contact pads 105, 205 of the substrate 101 and microfluidic component 201 respectively.

The contact bumps 501 can be made from a resilient material such as a thermoplastic material or even a metal. The embodiments described above are described by way of example only and do not limit the scope of protection in the claims as set out below.

REFERENCE NUMERALS

101 substrate
103 microfluidic channel
104 support structure
105 contact pads
106 electrical connection
107 additional support structure or micro bump
108 groove
110 substrate upper surface
111 access port
201 microfluidic component
202 lower surface
203 microfluidic channel
204 microfluidic component top surface
205 contact pad
211 access port
300 microfluidic device
309 adhesive
306 contact bump
400 device for applying adhesive to a stamp
401 rotatable stamp
402 drive shaft
403 adhesive dispenser
404 adhesive
406 dispensed adhesive
501 contact bump
502 raised contact structure
503 adhesive with contact bumps

What is claimed is:

1. A substrate for a microfluidic device, comprising:

at least one microfluidic structure having at least one access port at an upper surface of the substrate;

a first raised support structure positioned on the upper surface adjacent to each access port and surrounding the access port, the first raised support structure partially covering the substrate upper surface, the first raised support structure having an upper surface for receiving an adhesive for mounting a microfluidic component having at least one access port corresponding to the at least one access port of the substrate;

the substrate further comprising:

a pattern of second raised support structures for improving the mechanical bonding of the microfluidic component, the pattern of the second raised support structures having substantially a same height as the raised support structure, the second raised support structures having an upper surface for receiving the adhesive for mounting the microfluidic component;

wherein the pattern occupies a portion of the upper surface of the substrate not covered by the first raised support structure and/or the at least one access port;

wherein the pattern is evenly distributed over the portion of the upper surface not covered by the first raised support structure and/or the at least one access port; and wherein the second raised support structures have a square, rectangular or round shape as viewed in a top view.

2. The substrate according to claim 1, wherein the pattern of the second raised support structures comprises bumps.

3. The substrate according to claim 1, wherein each one of the second raised support structures has a width (W) and a height (H), the width (W) dimension being in approximately a range of 1-10 times the height (H) dimension.

4. The substrate according to claim 1, wherein the pattern of the second raised support structures comprises grooves between the second raised support structures.

5. The substrate according to claim 4, wherein the pattern is substantially a regular pattern.

6. The substrate according to claim 1, wherein the substrate material is a semiconductor material such as silicon.

7. The substrate according to claim 1, wherein the substrate material is a low corrosive material chosen from a group comprising glass, quartz, plastic, and epoxy.

8. A microfluidic device, comprising:

the substrate in accordance with claim 1;

a microfluidic component having at least one access port at a lower surface corresponding to the at least one access port of the substrate;

the microfluidic component being mounted on the top of the substrate with an adhesive applied between the upper surface of the first raised support structure and/or the second raised support structures and the lower surface of the microfluidic component.

9. The microfluidic device according to claim 8, wherein structures of the substrate upper surface match with corresponding structures of the microfluidic component bottom surface in accordance with flip-chip technology.

10. The microfluidic device according to claim 8, wherein the adhesive is applied between the upper surface of the first raised support structure and/or the second raised support structures and a corresponding surface of the microfluidic component only.

11. The microfluidic device according to claim 8, wherein the adhesive is at least one of a group of adhesives comprising epoxies, polyimide, high temperature ceramic adhesives, spin-on glass and glass frit.

12. The microfluidic device according to claim 8, further comprising an electrical connection of the substrate and the microfluidic component, the electrical connection comprising a contact bump, pressed between a contact pad of the substrate and a contact pad of the microfluidic component, wherein the adhesive layer has a thickness, wherein the thickness of the adhesive layer and a height of the at least one second raised support structure is adjusted to a size of the contact bump.

13. The microfluidic device according to claim 12, wherein the contact bump is made of gold.

14. The microfluidic device according to claim 8, wherein a contact pad of the substrate is arranged on a raised support structure, and the adhesive layer is provided with contact bumps, which contact bumps have a conductive outer layer.

15. The microfluidic device according to claim 14, wherein the contact bumps are made of a resilient material on which the conductive layer is provided.

16. The substrate according to claim 2, wherein each one of the second raised support structures has a width (W) and a height (H), the width (W) dimension being in approximately a range of 1-10 times the height (H) dimension, and wherein the pattern of the second raised support structures comprises grooves between the second raised support structures.

17. The substrate according to claim 16, wherein the pattern is substantially a regular pattern, wherein the substrate material is a semiconductor material such as silicon, and wherein the substrate material is a low corrosive material chosen from a group comprising glass, quartz, plastic, and epoxy.

18. The microfluidic device according to claim 9, wherein the adhesive is applied between the upper surface of the first raised support structure and/or the second raised support structures and a corresponding surface of the microfluidic component only, and wherein the adhesive is at least one of a group of adhesives comprising epoxies, polyimide, high temperature ceramic adhesives, spin-on glass and glass frit.

19. The microfluidic device according to claim 18, further comprising an electrical connection of the substrate and the microfluidic component, the electrical connection comprising a contact bump, pressed between a contact pad of the substrate and a contact pad of the microfluidic component, wherein the adhesive layer has a thickness, wherein the thickness of the adhesive layer and a height of the at least one second raised support structure is adjusted to a size of the contact bump, and wherein the contact bump is made of gold.

20. The microfluidic device according to claim 19, wherein a contact pad of the substrate is arranged on a raised support structure, and the adhesive layer is provided with contact bumps, which contact bumps have a conductive outer layer, and wherein the contact bumps are made of a resilient material on which the conductive layer is provided.

* * * * *